United States Patent [19]

Connors

[11] Patent Number: 5,177,424
[45] Date of Patent: Jan. 5, 1993

[54] INSTRUMENT HANDLE FOR USE WITH INTERCHANGEABLE BATTERIES

[75] Inventor: John D. Connors, Auburn, N.Y.

[73] Assignee: Welch Allyn, Inc., Skaneateles Falls, N.Y.

[21] Appl. No.: 763,142

[22] Filed: Sep. 20, 1991

[51] Int. Cl.⁵ .................. H01M 10/44; H02K 7/14
[52] U.S. Cl. ........................................ 320/2; 310/50
[58] Field of Search .................. 320/2, 15; 30/500; 310/50; 128/4, 9

[56] References Cited

U.S. PATENT DOCUMENTS

| | | | |
|---|---|---|---|
| 3,096,941 | 1/1960 | Miller | 320/2 |
| 3,201,742 | 8/1965 | English | 320/2 |
| 3,281,637 | 9/1963 | Hultquist | 320/2 |
| 4,147,163 | 4/1979 | Newman et al. | 128/9 |
| 4,382,219 | 5/1983 | Heine et al. | 320/2 |
| 4,751,452 | 6/1988 | Kilmer et al. | 320/2 |
| 4,782,432 | 11/1988 | Coffman | 362/184 |
| 5,008,785 | 4/1991 | Maglica et al. | 362/183 |
| 5,019,767 | 5/1991 | Shirai et al. | 320/2 |

Primary Examiner—William H. Beha, Jr.
Assistant Examiner—Matthew Nguyen
Attorney, Agent, or Firm—Wall and Roehrig

[57] ABSTRACT

A battery operated medical instrument that can operate on either rechargeable or non-rechargeable batteries or can be recharged using either a 120 Volt or a 220 Volt outlet.

7 Claims, 3 Drawing Sheets

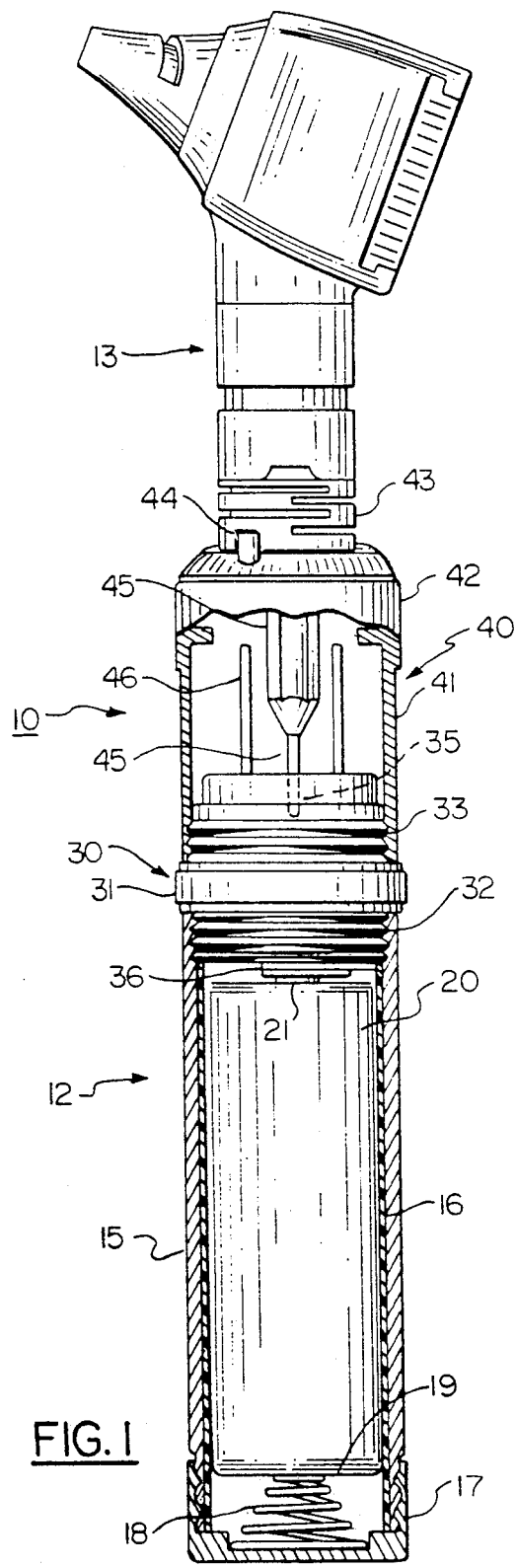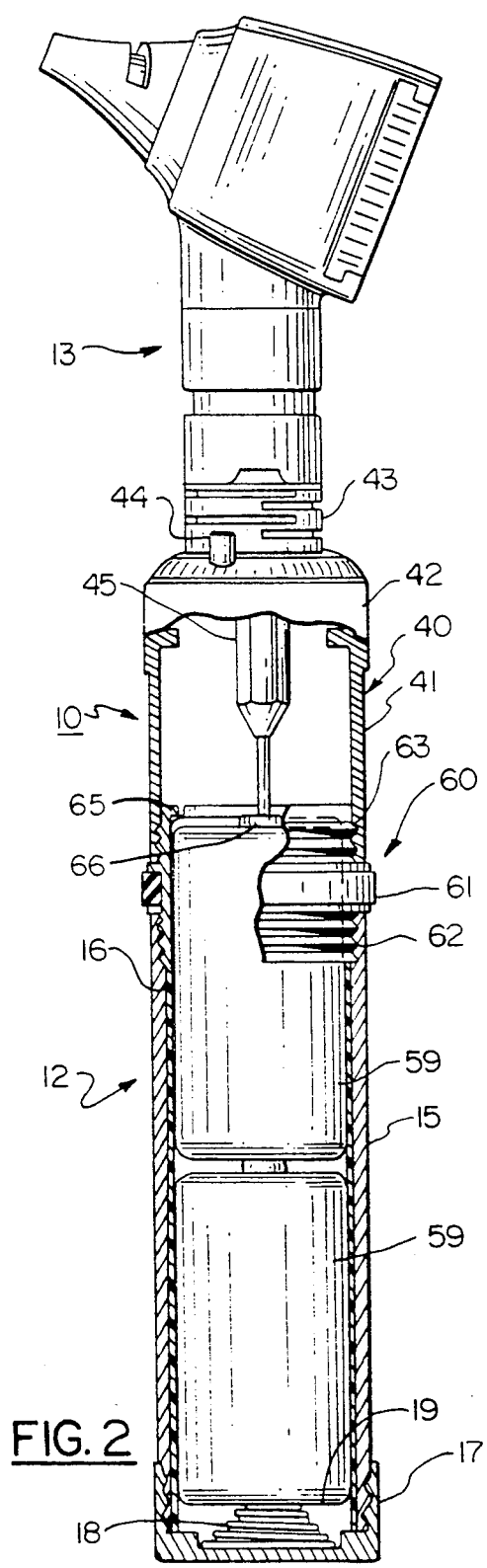

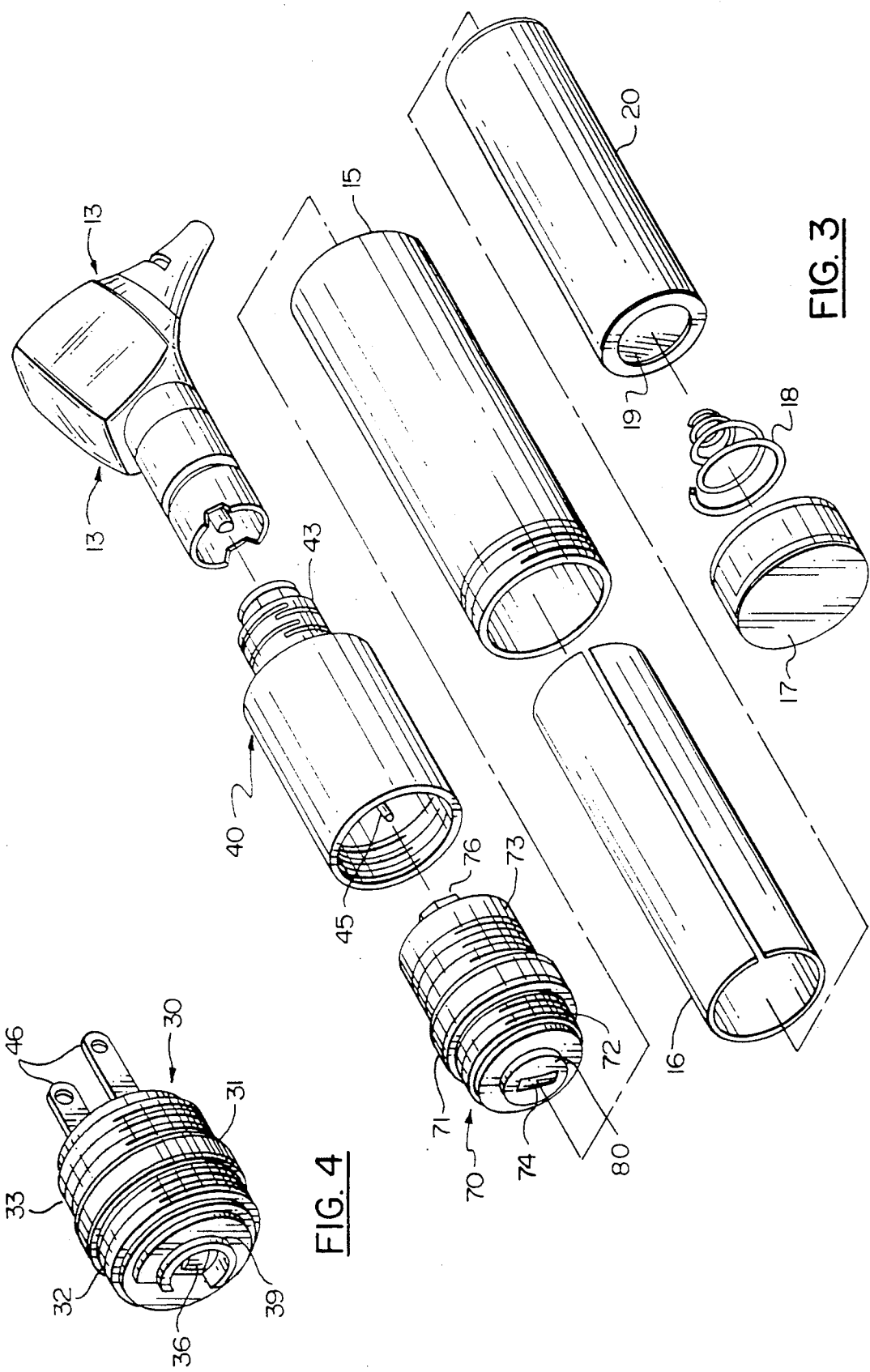

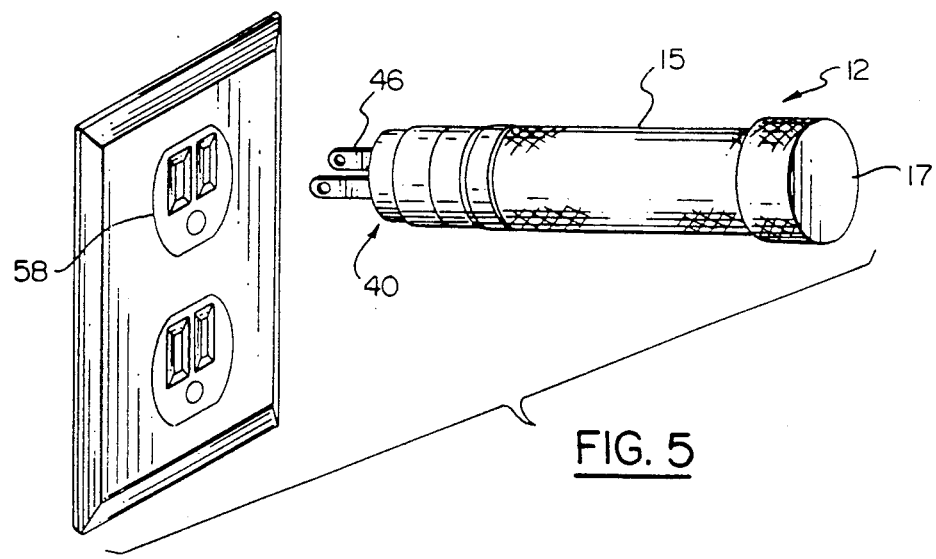
FIG. 5
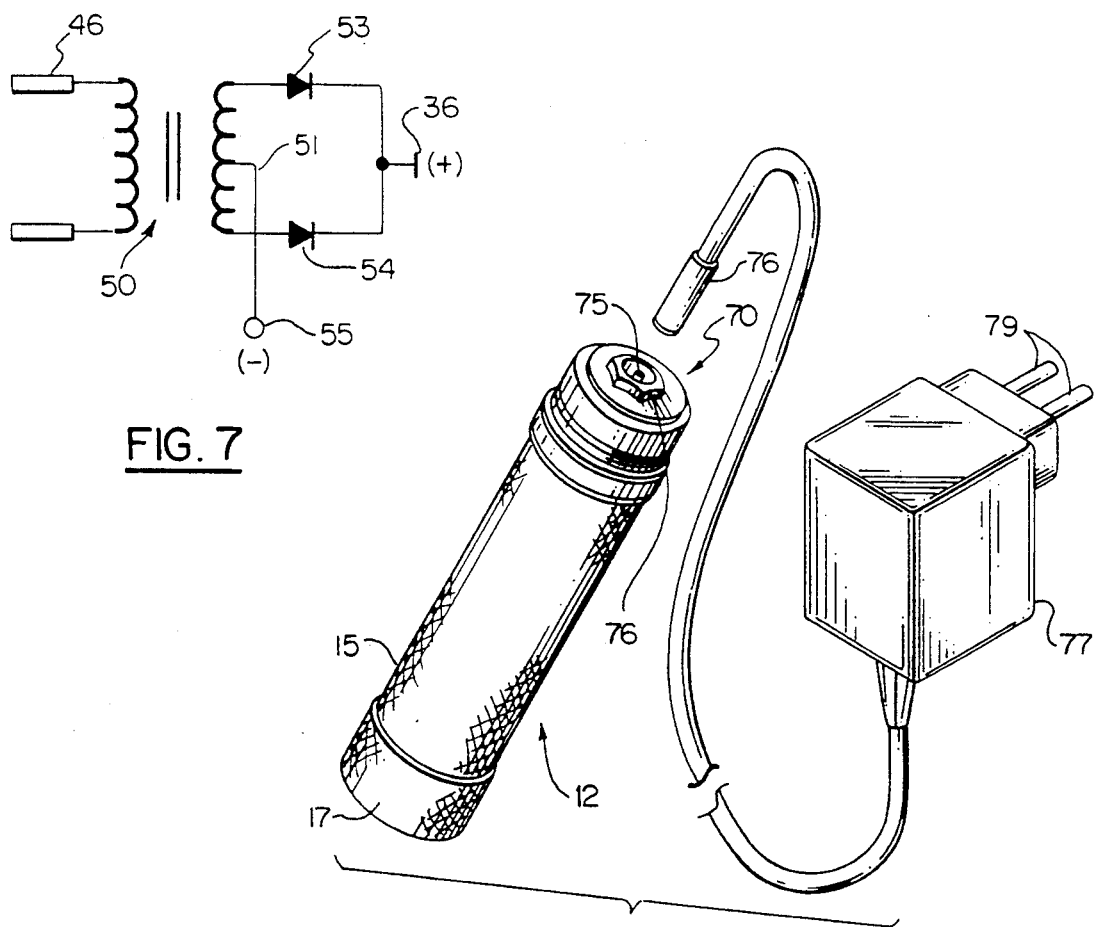
FIG. 7
FIG. 6

INSTRUMENT HANDLE FOR USE WITH INTERCHANGEABLE BATTERIES

BACKGROUND OF THE INVENTION

This invention relates to a battery handle which may be connected interchangeably to a variety of electrically dependent instruments. More specifically, this invention deals with such a handle which may accept either two non-rechargeable batteries, or a single rechargeable battery having different lengths. When using a rechargeable battery, the unit may be recharged either by directly plugging the handle unit into a U.S. standard electrical outlet or by use of a suitable transformer as an intermediate.

Health professionals use a variety of small hand-held diagnostic instruments such as otoscopes, ophthalmoscopes and retinoscopes in order to perform a variety of functions. Optimal flexibility and portability is achieved by using battery operated versions of such instruments. The use of non-rechargeable batteries, however, is expensive, requires storage and frequent changes of batteries, and is environmentally unsound.

On the other hand, the use of rechargeable batteries that are recharged in separate rechargers is cumbersome and requires a fair amount of attention. Thus, having the ability to recharge a battery while it remains in the device is desirable, and has been incorporated into a number of devices, such as flashlights (U.S. Pat. Nos. 3,281,637 and 3,096,941).

However, such rechargeable units present a different problem in that prolonged use of the device drains the battery, which then takes a substantial amount of time to recharge. During the recharge period, which exceeds the time period of usability, the handle, and thus the instrument, is unusable. U.S. Pat. No. 4,147,163, assigned to present assignee, and U.S. Pat. No. 4,382,219 both address this problem by each providing a handle for a medical instrument that is capable of accepting either a rechargeable or non-rechargeable batteries.

Such dual battery units must overcome a number of potential problems. The first problem is that single or pairs of standard non-rechargeable batteries are not generally interchangeable with a rechargeable battery used in such instruments. A second problem is that an inadvertent attempt to charge a non-rechargeable battery can result in excessive heat, expansion of the battery, and the possible danger of an explosion. A third problem is that an inadvertent inversion of rechargeable batteries may result in a short circuit, destroying the batteries. A fourth problem is that when using a rechargeable battery having a side wall terminal, if this terminal is allowed to contact the handle, the handle will become excessively warm or even dangerously hot. A fifth problem associated with convertible battery handles stems from the fact that a single rechargeable battery and a pair of non-rechargeable batteries are of different lengths. In order to accommodate the different length combinations, the battery handle, typically, is overly long and the instrument attached thereto is unbalanced and difficult to manipulate, particularly by a person having small hands.

While some of these problems are addressed by the prior art, all of these problems are not handled. Also, two additional features are desirable. First it would be preferable for the unit to contain as few mechanically movable parts as possible, for ease and economy of production as well as for durability. Second, since the instruments involved may be used outside of the U.S., it is desirable for the handle to be adaptable to allow the batteries to be charged in other current/voltage combinations than those used within the U.S. by allowing direct linkage with a suitable transformer.

SUMMARY OF THE INVENTION

It is therefore a primary object of the present invention to provide a battery handle for use with interchangeable batteries, where such batteries may be either rechargeable or non-rechargeable.

Another object of this invention is to provide such an instrument which can be manufactured economically and efficiently and which is also sturdy and minimally subject to breakage of parts.

Still another object of this invention is to provide such an instrument where inadvertent acts such as inverting batteries or attempting to charge non-rechargeable batteries cannot be performed or, if performed, will not have harmful effects.

Another object of this invention is to provide such an instrument where rechargeable batteries may be recharged without using a charger distinct from the instrument itself.

It is a further object of this invention to provide such a handle where rechargeable batteries may be recharged using either a standard U.S. electrical outlet or via connection to a converter designed for use in a non-U.S. standard electrical outlet.

Yet another object is to provide a battery handle for powering an instrument that is not overly long and which is well balanced and easily manipulated by a person having small hands.

These and other objects of the present invention are attained by a battery operated medical instrument having a battery handle that accepts a number of interchangeable adaptors which enable the instrument to operate with either rechargeable batteries or non-rechargeable batteries. When utilizing rechargeable batteries, the batteries can be recharged safely without having to remove them from the handle. The batteries can be recharged using a standard U.S. 120 Volt outlet or a foreign 220 Volt outlet.

BRIEF DESCRIPTION OF THE DRAWING

For a better understanding of these and other objects of the present invention, reference shall be made to the following detailed description of the invention which is to be read in conjunction with the accompanying drawings, wherein:

FIG. 1 is a side elevation in partial section showing a diagnostic medical instrument embodying the teachings of the present invention that includes a battery handle having an interchangeable adaptor that allows for the use of a rechargeable battery, the adaptor further includes a transformer that is in association with a conventional 120 Volt outlet so that the battery can be recharged without having to remove it from the handle;

FIG. 2 is a side elevation of the instrument shown in FIG. 1 wherein the handle is equipped with a second interchangeable adaptor that permits the instrument to operate on non-rechargeable batteries;

FIG. 3 is an exploded view in perspective of the instrument wherein the handle is equipped with a third interchangeable adaptor that permits a rechargeable battery contained in the handle to be recharged using a 220 Volt outlet;

FIG. 4 is also a perspective view of the adaptor shown in FIG. 1 further illustrating the construction thereof;

FIG. 5 is a perspective view of the battery handle shown in FIG. 1 being plugged into a standard U.S. outlet;

FIG. 6 is a further perspective view of the battery handle shown in FIG. 3 being connected to an independent transformer so that the battery can be recharged using a non-U.S. outlet; and FIG. 7 is a schematic diagram of the ac to dc converter used in association with the adaptor shown in FIG. 1.

DESCRIPTION OF THE INVENTION

Referring initially to FIG. 1, there is shown a battery-powered diagnostic medical instrument generally referenced 10. The instrument contains two main sections; a battery handle 12 and an instrument head 13 that is removably attached to the handle. The instrument head in this case is an otoscope, however, the handle can be used interchangeably with any number of instrument heads as presently marketed by Welch Allyn, Inc. of Skaneateles Falls, N.Y. Typically, the head will minimally contain a light source for illuminating the region being examined.

The battery handle includes a tubular battery casing 15 made of a conductive metal that serves as an electrical ground in the battery powered circuit. The lower or proximal end of the battery casing is closed by an end cap 17 that is removably threaded onto the casing. The end cap contains a helically-wound compression spring 18 that is adapted to contact the bottom surface or negative terminal 19 of a battery 20 housed inside the casing and thus connect the negative terminal to ground. In this embodiment of the invention, a rechargeable battery 20 is employed.

Rechargeable batteries of this type are disclosed in U.S. Pat. No. 3,220,888 owned by the present assignee. Rechargeable batteries of this type all contain a centrally-positioned, positive terminal 21 mounted in the top wall thereof. The negative terminal, however, may either be situated in the lower or proximal wall as shown in FIG. 1, or, alternatively protrude outwardly from the side of the battery to make contact directly against the inner wall of the handle casing. As will become apparent from the disclosure below, a rechargeable battery with a side protruding negative terminal could inadvertently be placed in the present handle casing. In this situation, the positive terminal of the battery contacts spring 18 and negative side terminal contacts the casing thus shorting the battery to ground. When this occurs, the handle becomes extremely warm and can pose a hazard to anyone touching it. A non-conductive sleeve 16 is contained within the casing which prevents a rechargeable battery having a side protruding negative terminal from electrically contacting the casing and thus shorting out the battery.

Referring to FIGS. 1 and 4, an adaptor 30 is threaded onto the top of the battery casing 15. The adaptor, as shown in FIG. 4, includes a centrally located flange 31, a lower or proximal threaded section 32 which is threaded into the casing and an upper or distal threaded section 33 which is threaded into a connector housing 40. The connector housing has a tubular body 41 that is adapted to mate with the upper threaded section of adaptor 30 and further includes an end closure 42 upon which is supported an axially-extended coupling 43.

Otoscope 13 is shown in FIG. 1 attached to the coupling in an operative position. A switch 44 is located in the end closure of the connector housing which functions to open and close the electrical path between the instrument head and a pin connector probe 45. The pin connector extends downwardly i.e., proximally from the end closure into the housing where it is received within a socket 35 located in the top wall of the adaptor 30. Although not shown, the socket is electrically connected to an electrical pad 36 mounted on the bottom wall of the adaptor. The pad is arranged in assembly to make contact with the positive distal terminal 21 of the battery 20 and thus complete the circuit to provide electrical power to the instrument head.

Adaptor 30 has a pair of prongs 46—46 extending distally from the upper surface thereof. The prongs, in assembly, pass upwardly and are situated on either side of the pin connector 45. As illustrated schematically in FIG. 7, a self-contained ac to dc converter in the adapter 30 has the prongs electrically connected to the primary side of a transformer 50 mounted within the adaptor body. The secondary side of the transformer has a center tap 51 that is grounded directly to the handle casing through ground lead 55. Both sides of the secondary windings are connected to the pad 36 through diodes 53 and 54. The transformer is arranged to step down a 120 Volt AC input to the desired battery voltage on either side of the center tap. The output of the secondary windings are applied through the diodes to the battery in the form of a DC voltage.

Adaptor 30 has a C-shaped protective guard 39 that is arranged to surround the pad 36 and thus prevent the pad from contacting the negative, normally proximal end terminal of the rechargeable battery, in the event the battery is inserted into the casing in an inverted position. An inverted battery can electrically discharge through the transformer thereby causing the handle to become heated to produce a potentially hazardous condition. More importantly, the battery itself can become overheated during a recharging cycle which again poses a danger to anyone handling the device.

To recharge the battery, the adaptor connector housing is unscrewed from the adaptor to expose the electrical prongs 46—46 and the prongs are then connected as illustrated in FIG. 5 into any conventional 120 Volt outlet 58 for a sufficient period of time to bring the battery up to its operating level.

Turning now to FIG. 2, the instrument, as described with reference to FIG. 1, is shown adapted to operate on two non-rechargeable batteries 59—59 in place of the single rechargeable battery 20. In this embodiment of the invention, adaptor 30 has been replaced with a second adaptor 60. Adaptor 60, like the first adaptor 30, includes a flange 61, a lower threaded section 62 that is threaded into the battery casing 15 and an upper threaded section 63 that is threaded into the connector housing 40. In this embodiment of the invention, the rechargeable battery is replaced by two standard size C-cells. The combined length of the two C-cells is greater than the length of the rechargeable battery 20. However, the C-cells cannot be recharged, and therefor the need for a transformer is eliminated. The interior of the adaptor is hollow to receive the uppermost battery in the stack. The top wall 65 of the adaptor contains a central opening in which the positive terminal 66 of the uppermost battery is received. Spring 18 urges the cell stack upwardly so that the terminal 66 is biased into contact with pin 45 thus completing the electrical power circuit to the instrument head.

As should be evident from the disclosure above, an instrument embodying the present invention can be quickly converted by a physician or healthcare worker to operate on relatively inexpensive, throw-away batteries in an emergency situation or when there is insufficient time to wait for the rechargeable battery to be charged.

FIG. 3 is an exploded view showing the component parts of the present invention. In this particular embodiment of the invention, a third adaptor 70 is employed which permits the rechargeable battery 20 to be recharged using a 220 Volt outlet, or the like, as found in many countries. Again, the adaptor 70 has a center flange 71, a lower threaded section 72 and an upper threaded section 73. A contact pad 74 is mounted in the bottom all of the adaptor which is arranged to make contact with the positive terminal of a battery contained in the battery casing. An insulating pad 80 surrounds the pad and prevents the pad from shorting against a battery that might be placed in the handle in an inverted position. The pad is electrically connected to lead 75 (FIG. 6) contained in socket 76 provided in the top wall of the adaptor. The lead is arranged to contact a pin similar to pin 45 noted above in the connector housing when the handle is assembled with the instrument head. As illustrated in FIG. 6, the handle can be separated at the adaptor from the connector housing. When separated, the socket and lead in the top of the adaptor are exposed so that the handle can be plugged into the receptor 76 of a 220 Volt transformer 77. The transformer contains prongs 79—79 that are specially adapted for insertion into a standard 220 Volt outlet used in many foreign countries.

While this invention has been explained with reference to the structure disclosed herein, it is not confined to the details as set forth and this application is intended to cover any modifications and changes as may come within the scope of the following claims.

What is claimed is:

1. A battery diagnostic handle for use in powering an instrument, and which is adapted to operate with either a rechargeable battery or non-rechargeable cells each having terminals of opposite polarities disposed at proximal and distal ends thereof, that comprises a hollow member that is closed at a proximal end thereof by an end cap having an electrical ground resiliently biased into contact with a proximal terminal of a battery contained in said hollow member, said hollow member being capable of interchangeably housing either a rechargeable battery or a stack of non-rechargeable cells a first adaptor means, for use when said non-rechargeable cells are used, and a second adaptor means, for use when said rechargeable battery is used, interchangeably mountable on a distal end of said hollow member, a connector housing removably attached to either of said adaptors for removably mounting an instrument head to said hollow member, said connector housing containing an axially elongated connector probe, said first adaptor means having positioning means for receiving a distal portion of a non-rechargeable cell contained in said hollow member and a central opening through which said connector probe makes contact with a distal terminal of a non-rechargeable cell positioned in said first adaptor means, said second adaptor means including a contact pad for contacting a distal terminal of a rechargeable battery contained in said hollow member and means for receiving said connector probe and electrically connecting said connector probe to said pad, ac to dc converter means electrically coupled to said pad, a pair of prongs connected to a primary side of said converter means and extending distally on either side of the connector probe whereby the handle can be plugged into a conventional outlet, when it is detached from the connector housing, to recharge said rechargeable battery.

2. The battery handle of claim 1 that further includes a third interchangeable adaptor having a socket means and a further converter means removably connectable to the socket means whereby a rechargeable battery housed in said member is chargeable from a non-conventional outlet.

3. The battery handle of claim 2 wherein said adaptors are threaded at both ends to mate with internal threads formed in both the member and the connector housing.

4. The battery handle of claim 1 that further includes an electrically non-conductive sleeve lining an interior side wall surface of said hollow member whereby a battery of the type having a side terminal is prevented from providing current through said side wall surface of said hollow member.

5. The battery handle of claim 1 wherein the second adaptor means has an electrically non-conductive collar surrounding the contact pad, said collar having a height such that said proximal terminal of a battery cannot come in contact with said pad when said battery is mounted in an inverted position within said hollow member.

6. The battery handle of claim 1 wherein said ground contained in said end cap is a helically wound compression spring.

7. The battery handle of claim 1 wherein said end cap is removably attached onto said hollow member.

* * * * *